United States Patent
Forzani et al.

(10) Patent No.: US 9,931,055 B2
(45) Date of Patent: Apr. 3, 2018

(54) MOUTHPIECE FOR ACCURATE DETECTION OF EXHALED NO

(71) Applicant: Arizona Board of Regents on behalf of Arizona State University, Scottsdale, AZ (US)

(72) Inventors: Erica Forzani, Mesa, AZ (US); Nongjian Tao, Fountain Hills, AZ (US); Xiaojun Xian, Gilbert, AZ (US); Francis Tsow, Tempe, AZ (US)

(73) Assignee: ARIZONA BOARD OF REGENTS ON BEHALF OF ARIZONA STATE UNIVERSITY, Scottsdale, CA (US)

( * ) Notice: Subject to any disclaimer, the term of this patent is extended or adjusted under 35 U.S.C. 154(b) by 292 days.

(21) Appl. No.: 14/431,730

(22) PCT Filed: Sep. 27, 2013

(86) PCT No.: PCT/US2013/062151
§ 371 (c)(1),
(2) Date: Mar. 26, 2015

(87) PCT Pub. No.: WO2014/052741
PCT Pub. Date: Apr. 3, 2014

(65) Prior Publication Data
US 2015/0201865 A1    Jul. 23, 2015

Related U.S. Application Data

(60) Provisional application No. 61/707,070, filed on Sep. 28, 2012.

(51) Int. Cl.
*A61B 5/08* (2006.01)
*A61B 5/097* (2006.01)
(Continued)

(52) U.S. Cl.
CPC .............. *A61B 5/082* (2013.01); *A61B 5/087* (2013.01); *A61B 5/097* (2013.01); *G01N 33/497* (2013.01)

(58) Field of Classification Search
CPC .......... A61B 5/082; A61B 5/087; A61B 5/097; G01N 33/497
See application file for complete search history.

(56) References Cited

U.S. PATENT DOCUMENTS 6,010,459 A    1/2000  Silkoff et al.
6,038,913 A *  3/2000  Gustafsson .......... A61B 5/0813
                                                        600/531
(Continued)

FOREIGN PATENT DOCUMENTS

DE    3844455 A1    8/1989
EP    0650051 A2    4/1995
(Continued)

OTHER PUBLICATIONS

Silkoff et al., Marked flow-dependence of exhaled nitric oxide using a new technique to exclude nasal nitric oxide, Am J Respir Crit Care Med, Jan. 1997, 260-7, vol. 155, No. 1.
(Continued)

*Primary Examiner* — Puya Agahi
(74) *Attorney, Agent, or Firm* — George A. Leone; Citadel Patent Law

(57) ABSTRACT

A low back pressure mouthpiece for accurate detection of exhaled nitric oxide (NO) includes a conduit for receiving the exhaled breath from the subject. An oxidizing filter for sample conditioning, wherein the conduit and oxidizing filter operate to produce a back pressure of less than 4 cm $H_2O$; and a device for measuring the level of one or more components of the received exhaled breath.

12 Claims, 9 Drawing Sheets

(51) Int. Cl.
   *A61B 5/087* (2006.01)
   *G01N 33/497* (2006.01)

(56) References Cited

U.S. PATENT DOCUMENTS

| | | |
|---|---|---|
| 2002/0193698 A1 | 12/2002 | Moilanen et al. |
| 2007/0240987 A1 | 10/2007 | Balakrishnan et al. |
| 2008/0107569 A1 | 5/2008 | Stefano et al. |
| 2008/0160477 A1* | 7/2008 | Stookey ............ A61B 1/00041 433/31 |
| 2010/0256514 A1* | 10/2010 | Chazan ................ G01N 21/783 600/532 |
| 2010/0282245 A1 | 11/2010 | Star et al. |
| 2012/0123288 A1 | 5/2012 | Van Kesteren et al. |

FOREIGN PATENT DOCUMENTS

| | | |
|---|---|---|
| EP | 0573060 B1 | 2/2000 |
| EP | 1075659 A1 | 2/2001 |
| EP | 0892926 B2 | 12/2006 |
| WO | 1995002181 A1 | 1/1995 |
| WO | 2009030957 A1 | 3/2009 |
| WO | 2014059158 A1 | 4/2014 |

OTHER PUBLICATIONS

Kharitonov et al., Exhaled and Nasal Nitric Oxide Measurements: Recommendations, Eur Respir J, Jul. 1997, 1683-93, vol. 10, No. 7.

Kharitonov et al., Nasal contribution to exhaled nitric oxide during exhalation against resistance or during breath holding, Thorax, Jun. 1997, 540-4, vol. 52, No. 6.

American Thoracic Society et al., ATS/ERS Recommendations for Standardized Procedures for the Online and Offline Measurement of Exhaled Lower Respiratory Nitric Oxide and Nasal Nitric Oxide, Am J Respir Crit Care Med, Apr. 2005, 912-30, vol. 171, No. 8.

Hogman et al., Nitric oxide from the human respiratory tract efficiently quantified by standardized single breath measurements, Acta Physiol Scand, Apr. 1997, 345-6, vol. 159, No. 4.

Malmberg et al., Exhaled nitric oxide rather than lung function distinguishes preschool children with probable asthma, Thorax, Jun. 2003, 494-9, vol. 58, No. 6.

Gustafsson et al., Endogenous Nitric Oxide is Present in the Exhaled Air of Rabbits, Guinea Pigs and Humans, Biochem Biophys Res Commun, Dec. 1991, 852-7, vol. 181, No. 2.

Persson et al., Single-breath nitric oxide measurements in asthmatic patients and smokers, Lancet, Jan. 1994, 146-7, vol. 343, No. 8890.

Matsumoto et al., Increased nitric oxide in the exhaled air of patients with decompensated liver cirrhosis, Ann Intern Med, Jul. 1995, 110-3, vol. 123, No. 2.

Kharitonov et al., Increased nitric oxide in exhaled air of asthmatic patients, Lancet, Jan. 1994, 133-5, vol. 343, No. 8890.

European Application No. 13841482.6, Extended European Search Report, dated Jun. 6, 2016.

* cited by examiner

Typical back pressure of the mouthpiece

MOUTHPIECE FOR ACCURATE DETECTION OF EXHALED NO

RELATED APPLICATION

This application claims priority from U.S. provisional application No. 61/707,070 of Forzani et al., filed Sep. 28, 2012, entitled "MOUTHPIECE FOR ACCURATE DETECTION OF EXHALED NO." U.S. application No. 61/707,070, is hereby incorporated by reference.

TECHNICAL FIELD

The present invention relates to a mouthpiece for accurate detection of exhaled nitric oxide (NO), this invention relates to the measurement of components of exhaled breath from the lower respiratory tract.

BACKGROUND

Exhaled pulmonary nitric oxide (NO) may aid in monitoring pulmonary disease. Unfortunately, it has been recognized that, in measuring exhaled pulmonary nitric oxide (NO), there are obstacles that must be overcome. For example, nasal NO concentration can be higher than alveolar NO concentration, and, as a result, contamination with Nasal NO may occur.

One attempt to provide a solution to this problem was as disclosed by Silkoff et al. in a paper entitled "Marked flow-dependence of exhaled nitric oxide using a new technique to exclude nasal nitric oxide," (AMERICAN JOURNAL OF RESPIRATORY AND CRITICAL CARE MEDICINE, Volume: 155, Issue: 1, Pages: 260-267, Published: January 1997). There a technique was developed to measure pulmonary NO, without nasal NO, by having the subject maintain a positive expiratory pressure (ensuring vellum closure) in an attempt to prevent contamination by nasal NO.

Unfortunately available techniques using exhalation against back pressure of 5 cm H2O or larger can be difficult for people with limited lung expiratory force. Such subjects exhibit an inability to maintain constant exhalation flow for several seconds (e.g., one commercially available device requires between 6 to 10 sec). Further, current commercial devices require pressure of 10-20 cm $H_2O$ to perform the measurement, which makes it difficult to get the measurement done, especially in children.

In contrast to known methods, now presented is a new and novel low back pressure mouthpiece for measuring NO that overcomes difficulties in this area not adequately addressed until now.

BRIEF SUMMARY OF THE DISCLOSURE

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A low back pressure mouthpiece for accurate detection of exhaled nitric oxide (NO) comprising:

conduit means for receiving the exhaled breath from the subject;

an oxidizing filter means coupled to the conduit means for sample conditioning, wherein the oxidizing filter means has an outlet and wherein the conduit means and oxidizing filter means operate to produce a back pressure of less than 4 cm $H_2O$; and means for measuring the level of one or more components of exhaled breath received from the outlet.

BRIEF DESCRIPTION OF THE DRAWINGS

While the novel features of the invention are set forth with particularity in the appended claims, the invention, both as to organization and content, will be better understood and appreciated, along with other objects and features thereof, from the following detailed description taken in conjunction with the drawings, in which:

Figure 1A:
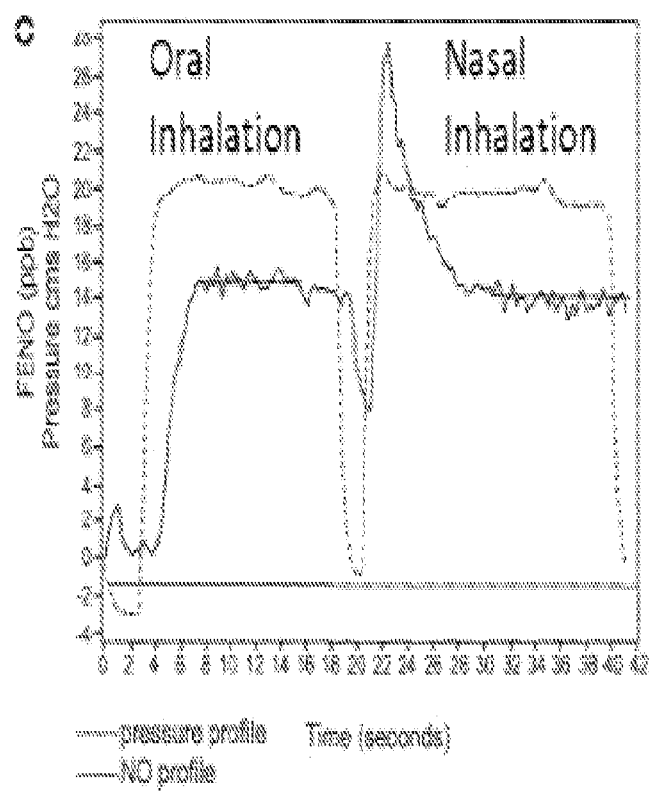
FIG. 1A shows a graphical illustration of exhaled NO measurements.

In the drawings, identical reference numbers identify similar elements or components. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION OF THE PREFERRED EMBODIMENTS

The following disclosure describes several embodiments for a low back pressure mouthpiece for NO measurement. Several features of methods and systems in accordance with example embodiments are set forth and described in the Figures. It will be appreciated that methods and systems in accordance with other example embodiments can include additional procedures or features different than those shown in the Figures. Example embodiments are described herein with respect to analysis of pulmonary NO. However, it will be understood that these examples are for the purpose of illustrating the principles, and that the invention is not so limited. Additionally, methods and systems in accordance with several example embodiments may not include all of the features shown in the Figures.

Unless the context requires otherwise, throughout the specification and claims which follow, the word "comprise" and variations thereof, such as, "comprises" and "comprising" are to be construed in an open, inclusive sense that is as "including, but not limited to."

Reference throughout this specification to "one example" or "an example embodiment," "one embodiment," "an embodiment" or combinations and/or variations of these terms means that a particular feature, structure or characteristic described in connection with the embodiment is included in at least one embodiment of the present disclosure. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Definitions

Generally, as used herein, the following terms have the following meanings when used within the context of sample collection or analysis:

As used herein, "plurality" is understood to mean more than one. For example, a plurality refers to at least 3, 4, 5, 70, or more.

As used herein, "cellular telephone" (or "smart phone") has its generally accepted meaning and includes any portable device that can make and receive telephone calls to and from a public telephone network, which includes other mobiles and fixed-line phones across the world. It also includes mobile devices that support a wide variety of other services such as text messaging, software applications, MMS, e-mail, Internet access, short-range wireless communications (for example, infrared and Bluetooth).

As used herein, "tablet computer" has its generally accepted meaning and includes any mobile computer including a complete mobile computer, larger than a mobile phone or personal digital assistant, integrated into a flat touch screen and primarily operated by touching the screen such as, for example, an Apple ipad® tablet computer.

Example Embodiments

The inventors here have noted their own experience with NO, and other's experience, including ATS/ERS indicate the nasal contamination (if present can be washed out). Referring now to FIG. 1A, a graphical illustration of exhaled NO measurements published by Kharitonov, "Exhaled and Nasal Nitric Oxide Measurements: Recommendations (Eur Respir J 1997, Vol. 10, pp. 1683-1693) illustrate the plateau of exhaled NO. According to this result, a back pressure of ~3 cm $H_2O$ (=2.3 mmHg) is sufficient to produce a stable NO plateau at the end of a breath.

Figure 1B:
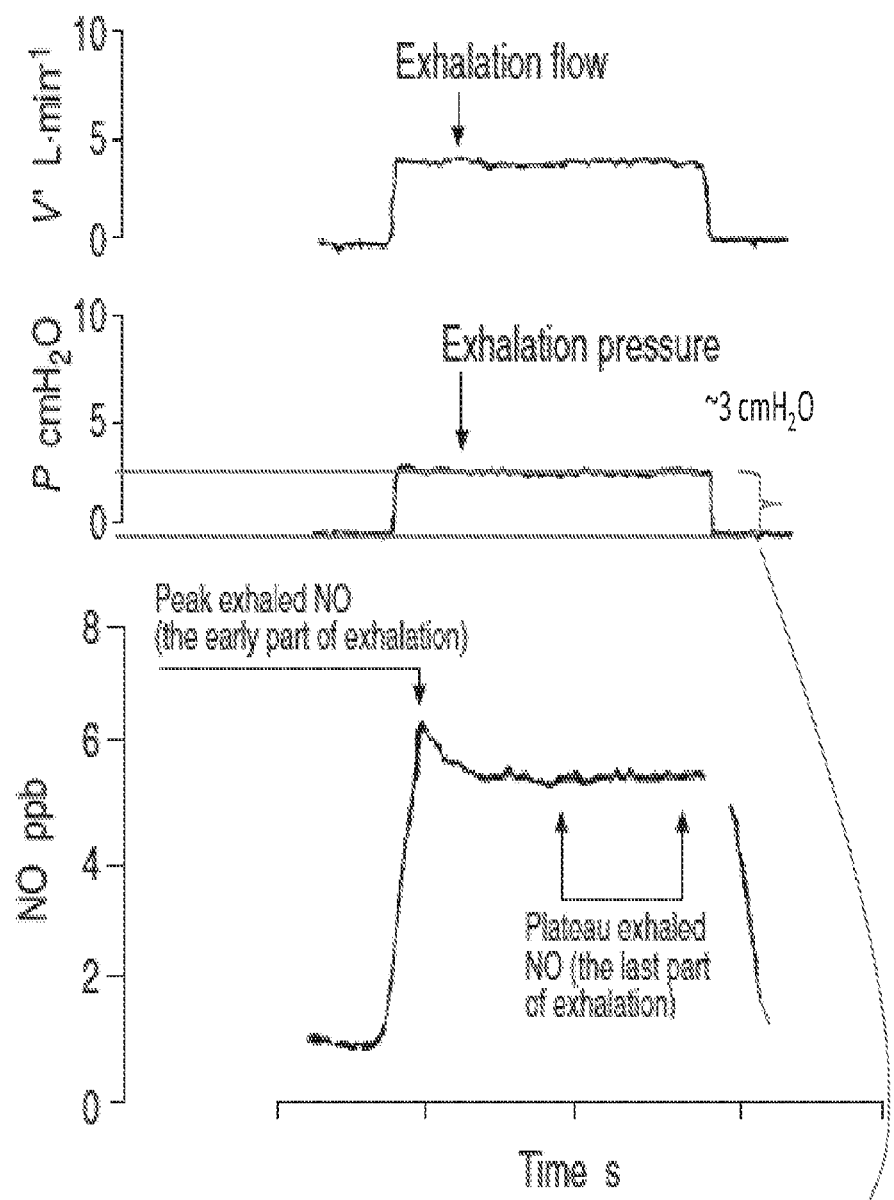
FIG. 1B shows a plot of NO concentration and airway opening vs. time as reported in a joint statement of the American Thoracic Society (ATS) and the European Respiratory Society (ERS).

Referring briefly to FIG. 1B, there shown is a plot of NO concentration and airway opening vs. time as reported in a joint statement of the American Thoracic Society (ATS) and the European Respiratory Society (ERS). See "ATS/ERS Recommendations for Standardized Procedures for the Online and Offline Measurement of Exhaled Lower Respiratory Nitric Oxide and Nasal Nitric Oxide, 2005," (Am J Respir Crit Care Med, Vol. 171, pp. 912-930, 2005). Note that in the exhaled NO pressure profile the NO plateau is essentially unaltered once the early peak has washed out. The inventor's here exploited their experience and the noted data to arrive at a new configuration of a low back pressure mouthpiece (herein referred to also as the "subject NO device" for measurement of exhaled NO).

Figure 2:
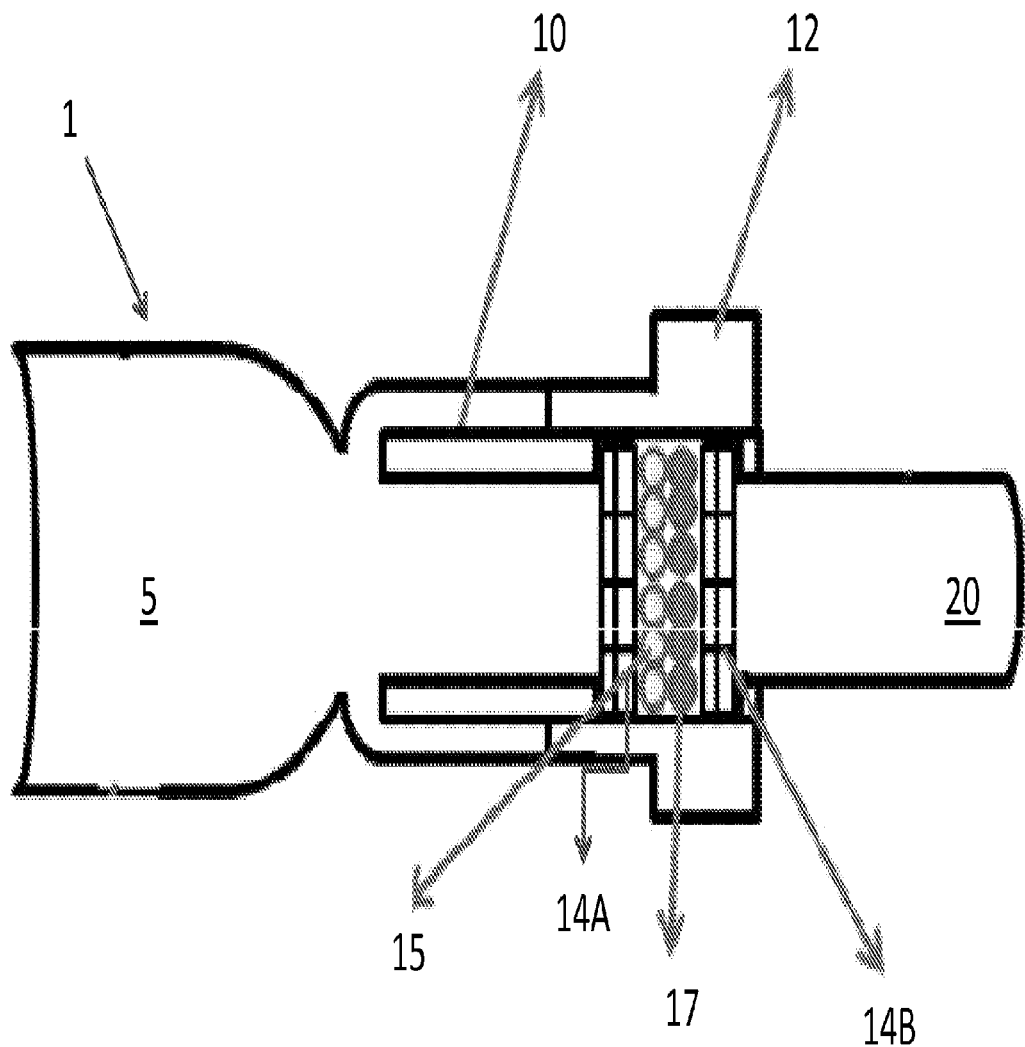
FIG. 2 schematically shows an example of a configuration and picture of a low back pressure mouthpiece.

Referring now to FIG. 2, an example of a low back pressure mouthpiece is schematically shown. A low back pressure mouthpiece apparatus 1 includes a breath inlet conduit 5, a coupler 10, an oxidizing filter housing 12, a first plurality of filters 14A, a second plurality of filters 14B and an outlet tube 20. Packed between the first and second plurality of filters 14A, 14B are at least two types of filtering particles including a first type of filtering particles 15 and a second type of filtering particles 17. In one useful embodiment the filter housing 12, first and second plurality of filters 14A, 14B and filtering particles 15, 17 perform as an oxidizing filter.

In one useful embodiment, the inner diameter of the filter housing 12 is at least 18 mm and the chemical particles are contained in the filter housing 12. In one useful embodiment the coupler 10 may be fabricated from an acrylic tube with inner diameter of at least 9.6 mm and outer diameter of at least 12.6 mm. The coupler 10 is used to guide the gas flow. In one embodiment, the first and second plurality of filters may advantageously comprise two felt pieces made from stiffened felt comprising about 100% Eco-fi, a high quality polyester fiber, with diameter of 18 mm. The filters are used as stoppers to retain the chemical particles within the mouthpiece filter housing. In a preferred embodiment the elements operate in a low back pressure range of less than 4 cm $H_2O$ and more preferably in a range from 1 to 3 cm $H_2O$.

In testing, as described in detail below, it has been shown that the mouthpiece has a capability of conditioning the breath at a flow of 50 ml/sec with an associated error of ±10% under sample collection condition with back pressure less than 4 cm $H_2O$. In one example embodiment, the breath inlet conduit 5 comprises a commercial mouthpiece element for sample collection. The oxidizing filter elements operate to provide sample conditioning. In one example embodiment, the oxidizing filter housing 12 was made from acrylic tubing with chemical particles packed inside. Two kinds of chemical particles were used in the oxidizing filter: 1) desiccant including 300 mg $CaSO_4$ (indicating drierite, stock number 23001, from W.A. HAMMOND DRIERITE CO., LTD.) for reducing the humidity in the breath; and 2) oxidant containing 300 mg of a solid porous substrate impregnated with sodium permanganate (available under the trade name Purafil®) to provide optimum gas oxidation. The Purafil® media works under a wide range of humidity levels (e.g. from 10% to 95% RH).

Further examples of useful desiccants include activated alumina, aerogel, benzophenone, bentonite clay, calcium chloride, calcium sulfate, cobalt(ii) chloride, copper(ii) sulfate, lithium chloride, lithium bromide, magnesium sulfate, magnesium perchlorate, molecular sieve, potassium carbonate, silica gel, sodium, sodium chlorate, sodium chloride, sodium hydroxide, sodium sulfate, sucrose and the like. Further examples of useful oxodizing agents include oxygen ($O_2$), ozone ($O_3$), hydrogen peroxide ($H_2O_2$) and other inorganic peroxides, fluorine ($F_2$), chlorine ($Cl_2$), and other halogens, nitric acid ($HNO_3$) and nitrate compounds, sulfuric acid ($H_2SO_4$), peroxydisulfuric acid ($H_2S_2O_8$), peroxymonosulfuric acid ($H_2SO_5$), chlorite, chlorate, perchlorate, and other analogous halogen compounds, hypochlorite and other hypohalite compounds, including household bleach (NaClO), hexavalent chromium compounds such as chromic and dichromic acids and chromium trioxide, pyridinium chlorochromate (PCC), and chromate/dichromate compounds, permanganate compounds such as potassium permanganate, sodium perborate, nitrous oxide ($N_2O$), silver oxide ($Ag_2O$), osmium tetroxide ($OsO_4$) and the like.

Figure 3:
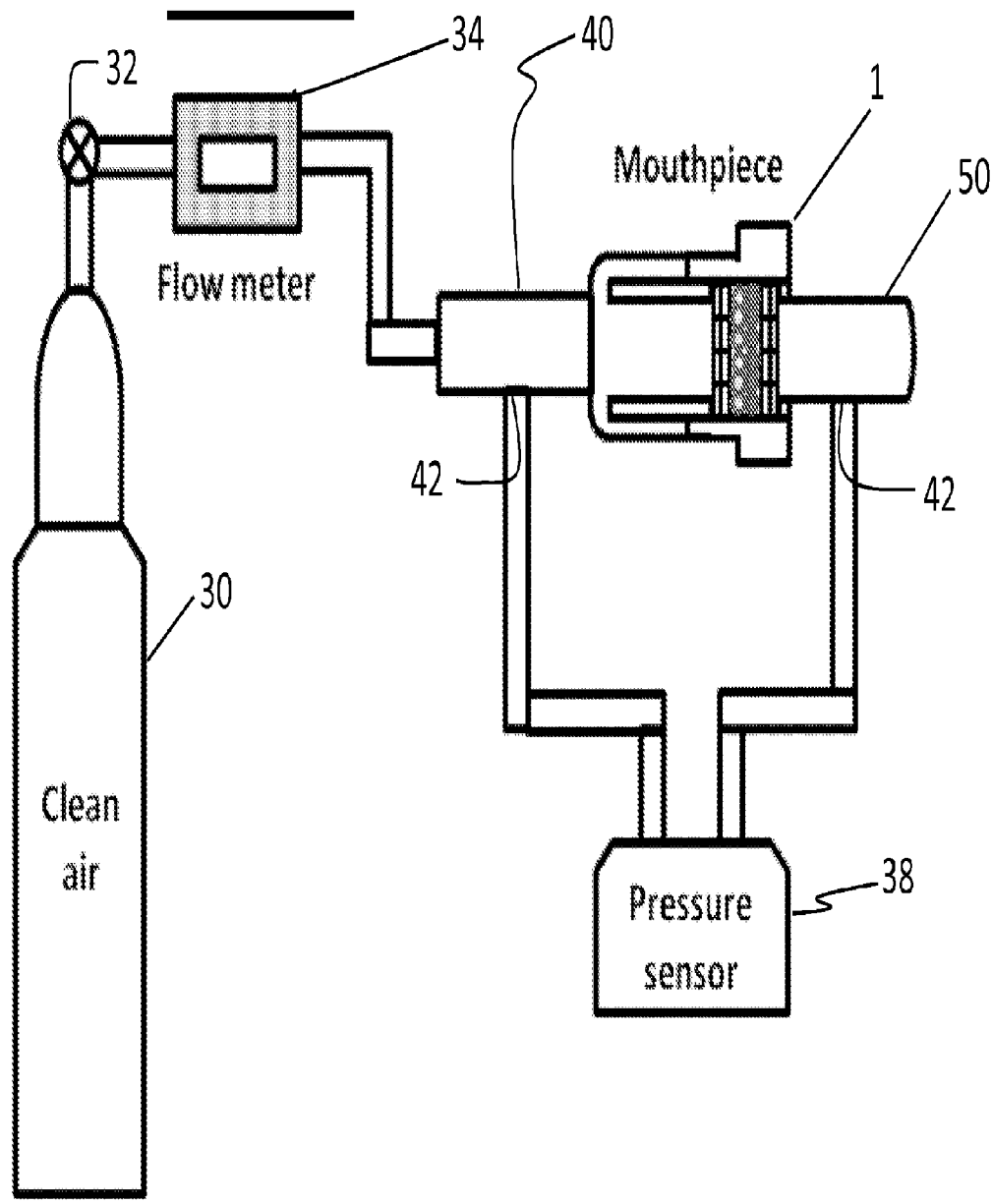
FIG. 3 shows a schematic representation of a test configuration for measuring back pressure across a mouthpiece.

FIG. 3 shows a schematic representation of a test configuration for measuring back pressure across a mouthpiece.

The test configuration includes a mouthpiece 1, a source of clean air 30, a valve 32, a flow meter 34 and a pressure sensor 38.

In one exemplary process, the back pressure across the mouthpiece 1 was measured by following the procedure below.

1) Connecting the source of clean air 30, such as a gas cylinder, and the flow meter in series to the inlet 7 of the mouthpiece 1;
2) Connecting the pressure sensor 38 across the mouthpiece 1 by drilling two holes in two acrylic tubes of same diameter in the mouthpiece at both inlet and outlet. The two probes of the pressure sensor are connected across the mouthpiece by using hard tubing;
3) Turning on the valve on the clean air gas cylinder and adjust the flow rate to be 50 ml/sec.; and
4) Obtaining the pressure drop readings from the pressure sensor.

Figure 4:
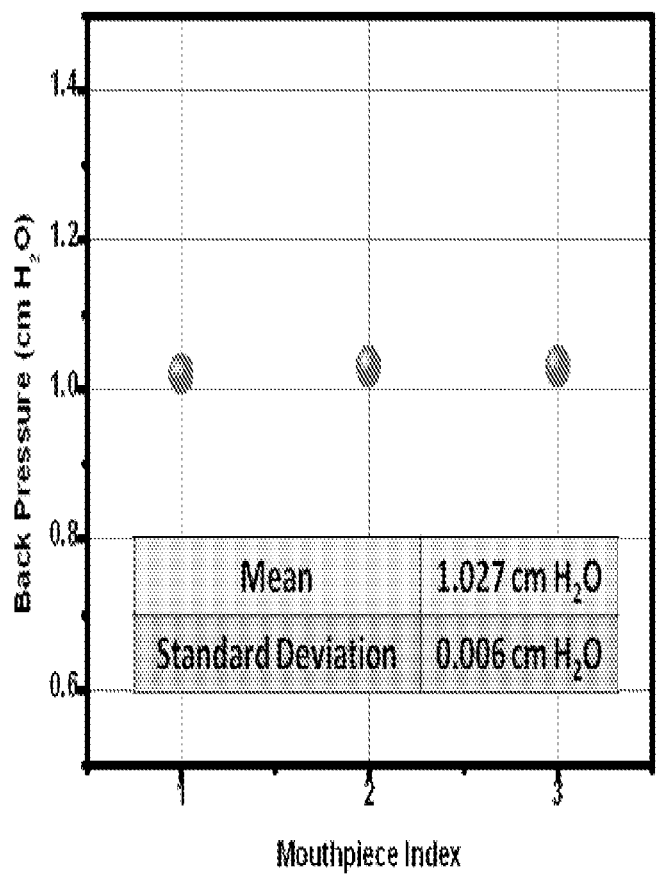
FIG. 4 graphically illustrates back pressure data of a mouthpiece.

Referring now to FIG. 4, typical back pressure data of a mouthpiece made in accordance with the teachings herein is graphically illustrated. In tests conducted by the inventors three individual mouthpieces were prepared and tested to get the back pressure data. In this example, the back pressure of one embodiment of the mouthpiece in cm $H_2O$ was plotted against the index of the mouthpiece and the mean and standard deviation was calculated. The results of the test were evaluated as acceptable if the back pressure of the mouthpiece is less than 4 cm $H_2O$ at a flow rate of 50 ml/sec. As shown for these tests the mean was 1.027 cm $H_2O$ with a standard deviation of 0.0006 cm $H_2O$.

Figure 5:
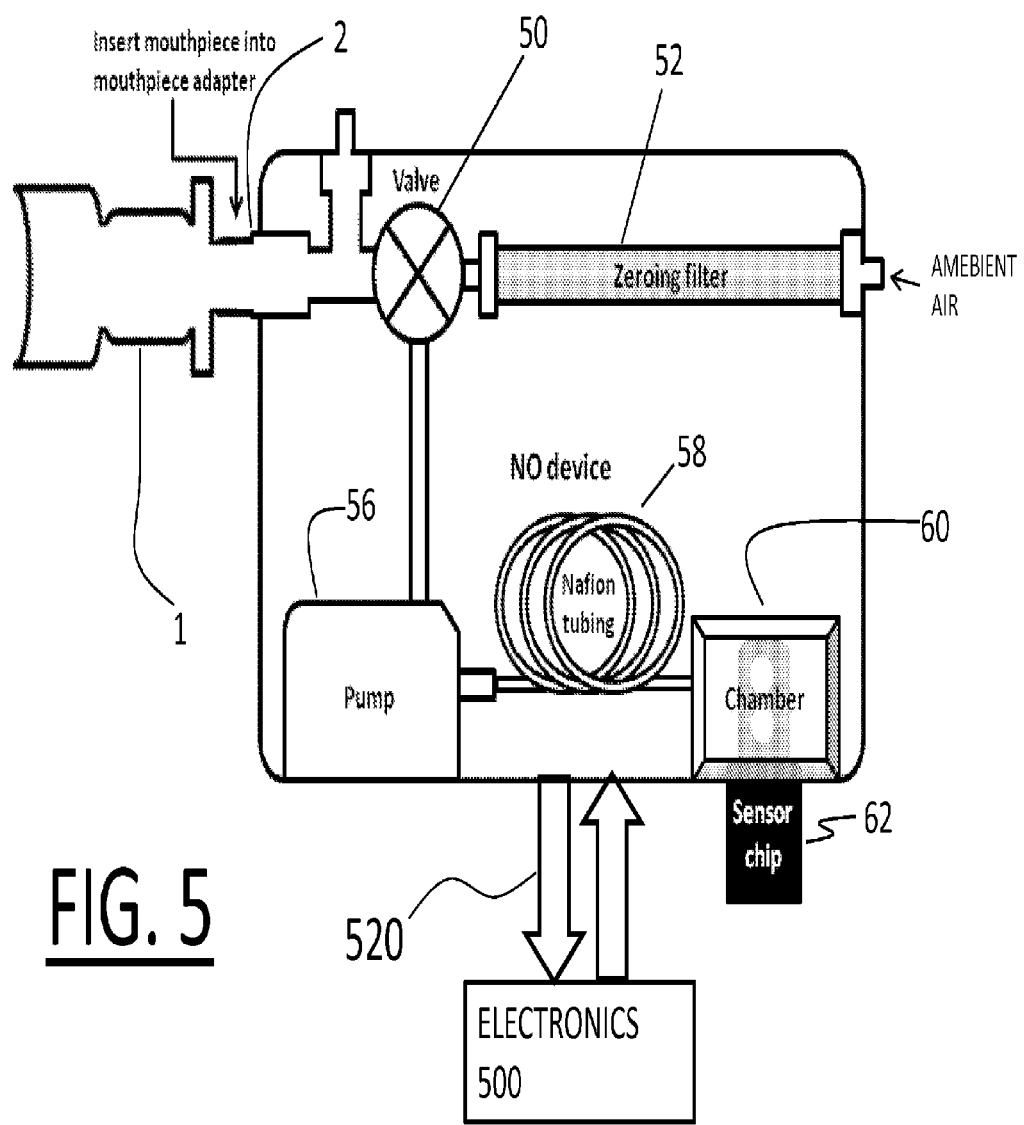
FIG. 5 schematically shows an example of an experimental configuration of a correlation test on an NO device.

Referring now to FIG. 5, an example of an experimental configuration of a correlation test on an NO device built in accordance with the principles disclosed herein is schematically shown. For the purposes of testing correlation an integrated NO device was constructed including a low back pressure mouthpiece 1, a valve 50, a zeroing filter 52, a pump 56, Nafion tubing 58, a sensor chip 62 within a sensor chamber 60, electronics on a printed circuit board (PCB) 500. Except for the new and novel low back pressure mouthpiece 1, the components may be standard components connected according to accepted engineering practice.

Figure 6:
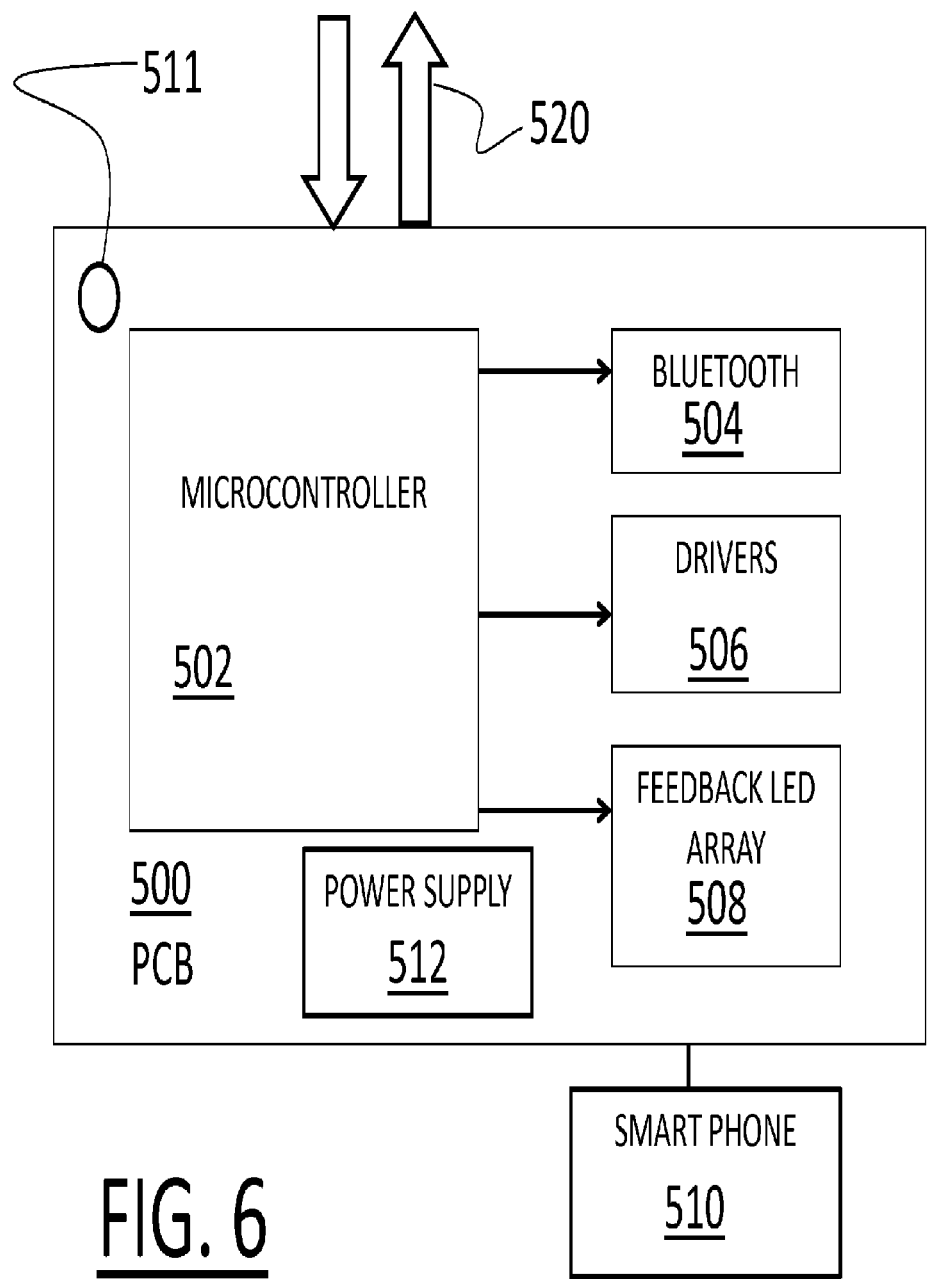
FIG. 6 schematically shows an example of electronics employed in an experimental configuration of a correlation test on an NO device.

Referring now to FIG. 6, an example of electronics employed in an experimental configuration of a correlation test on an NO device is schematically shown. The electronics 500 include a microcontroller 502, a Bluetooth transceiver 504, a plurality of drivers 506, a feedback LED array 508, a power supply 512, and a switch 511. The microcontroller and drivers operate to execute a software application in obtaining and storing data and communicating to a user. A smart phone 510 is employed in communication with the PCB 500 for data receiving, processing, and displaying. In one test an HTC HD2 Unlocked Phone with Windows Mobile 6.5 Professional was employed. The feedback LED array 508 comprised white, red, yellow and green LEDs in one example embodiment.

A software application written using standard computer science principles was installed in the smart phone to communicate with the Bluetooth of the NO device and display the test results. The application was written using Microsoft Visual Studio. In operation, the application asks the user to select the Bluetooth device from the list of devices that are visible to the phone. When the user selects the sensor device, the connection is established. The device sends out raw data for the reference channel and the sensing channel. The absorbance value is calculated by taking the negative of the logarithm value of the ratio of intensity of sensing to reference channel. Then the difference between the slope of sampling and the slope of purging is calculated. This difference value is the quantity that is related to the concentration of NO.

For correlation purposes chemiluminescence equipment used included a Nitric Oxide Analyzer (GE Analytical Instruments) Part number: NOA 280i. In one embodiment of the test setup the power supply comprised a commercially available battery charger, namely a TLP-2000 Tenergy Universal Smart Charger, from Tenergy Corp of Fremont, Calif., Part No. 01211.

A correlation test was performed to compare the accuracy between nitric oxide levels detected with subject sensor and with chemiluminescence method (made by Sievers and sold by GE Analytical, Boulder, Colo.—gold standard method recognized by FDA) and an existing commercial device. The results of the test are evaluated were considered acceptable if the correlation was larger than 90%.

Correlation of accuracy between the subject NO device and the gold standard method as well as the existing commercial device was completed by testing the NO level of real subjects. A new sensor chip and new mouthpiece is used for each test. In one test, nine different individuals were tested. Each subject may have been tested multiple times on different days or even at different times during the same day. For some subjects, their NO concentration may have been subject to change in a very broad range, for example from 30 ppb to 200 ppb, depending on the inflammation condition of their respiratory system. These subjects with more desirable NO concentration levels can be tested more.

Not all tests were completed on the same day and some over more than a month. One correlation test contains 65 data points. Each test consumed one mouthpiece and one sensor chip, so a total of 65 mouthpieces and 65 sensor chips were used for the correlation test. The device was scheduled for testing at ambient conditions, i.e. at room temperature, between 16° C. and 30° C., and a relative humidity (RH) between 20% and 60% (non-condensing).

Testing Procedure:

The following steps were performed for each test:
1) The batteries of the NO device were charged until they fully charged (tests were carried out without any external power supply).
2) The as prepared sensor chip was inserted into the sensor chamber of the NO device.
3) The switch was turned on and the device was warmed up for 20 minutes before the test.
4) During the warm up, test the NO level of the subject with commercial device and NO analyzer (the Chemiluminescence equipment) by following the corresponding instructions. One test may be performed on each device respectively and the results are used for correlation comparison since they are well established NO testing methods.
5) During the warm up, the mouthpiece was connected to the device via the mouthpiece adapter.
6) During the warm up, the ambient air was continuously sucked into the device through the zeroing filter for purging and the white LED was always on to indicate the warm-up was ongoing.
7) During the warm up, the software was run on the smart phone to communicate with the NO device. During the warm up, the smart phone may display "measuring" on the screen.
8) Once the warm-up was finished, the white LED was automatically off and yellow LED turned on.
9) The subject being tested then placed their mouth on the mouthpiece and blew. During the test, once a subject began supplying a sample within the correct flow rate window the green LED turned on. When the green LED was on the sampling time lasted for 6 seconds, during which time the subject must keep their breath at the correct flow rate for at least 6 seconds.

10) Note that if the subject was unable to make the flow rate in range, a red or yellow LED was turned on to give the subject feedback. If the red LED turned on, it indicated that the flow rate was too high and the subject must reduce their breath flow rate. Conversely, if the yellow LED turned on, it indicated that the flow rate was too low and the subject must increase their breath flow rate. A 10 second time window was set for the subject to adjust their breath flow rate. If the subject could not keep the flow rate in range for 6 seconds within this 10 second time window, the device would go back to baseline and purge the system for 60 seconds. At this time all the three LED indicators (red, green and yellow) would be turned off. Once the new baseline was built, the yellow LED would be turned on again and the subject can try to blow and do the test again.

11) Should the subject complete a test by holding the correct flow rate (maintaining the green LED lit) for 6 seconds continuously, the sampling period ended. All the LEDs (include white, red, green, and yellow) would automatically be turned on, which indicated that the NO device was sending data to the smart phone. The smart phone will continue to display "measuring" during this time. The subject can stop breath when all the LEDs are turn on.

12) When the data transmission was completed the smart phone screen would change to display concentration and temperature. This concentration value was calculated by using the given calibration curve in the smart phone application. In this case, since the given calibration curve was based on the artificial sample tests, which may be diverse a little bit from the real breath test, the displayed concentration for the correlation comparison was not used. Instead, the real sensor response was calculated according the procedure mentioned in the data analysis section. The temperature value displayed was not a real breath temperature (it was a fixed value).

13) To complete the second test on the same sensor cartridge the device was not turned off and the sensor chip was left in the same position. The warm-up did not need to take place again as the device was left on. The mouthpiece was left in position as well. The smart phone application would need to be restarted by quitting the application from the smart phone then re-opening the application. When again connecting to the device, the smart phone screen will again display "measuring" once connected. Wait until the test was done.

14) Step 13 was repeated for a third test on the same sensor chip.

15) A predetermined "r" value correlation coefficient check function was integrated into the software program so that the smart phone application would automatically check the "r" value (correlation coefficient) of the data obtained to evaluate the quality of the test. If the "r" value was lower than a predetermined threshold, the application will display "test fail" on the screen, which means this test should not be considered as an acceptable measurement and a new test need to be carried out.

16) The device was turned off and a new mouthpiece was prepared while a new sensor chip was inserted into the chamber of the NO device. The test steps would be repeated from steps 3 to 14 with a new test subject to provide a different concentration level. If necessary the batteries of the device were charged. A fully charged device should be able to test three different sensor chips.

Data Analysis

Figure 8:
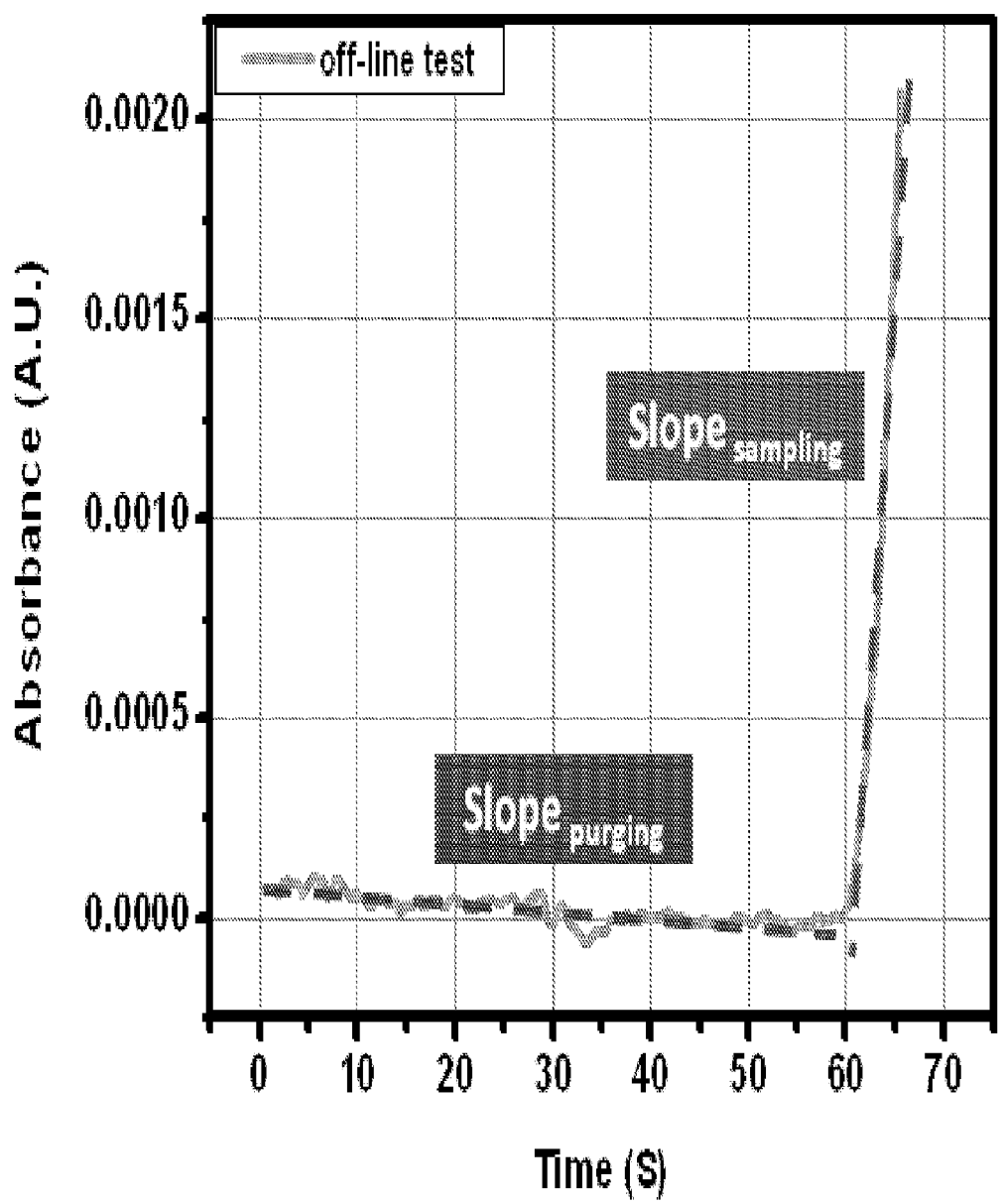
FIG. 8 shows a typical plot of sensor response for one cycle of test with purging and sampling periods.

The raw data of each test was transmitted and automatically saved in the smart phone. In order to get a more accurate concentration, the concentration displayed on the phone was not used as the final result because it was based on the calibration curve obtained from artificial sample tests. The procedure below was followed for the data analysis:

1) The raw data with txt format was copied from the smart phone and saved in a personal computer for data processing.
2) A txt file was opened with Origin (a common scientific data analysis software available from OriginLab of Northampton, Mass.), the unit of time was changed from HH:MM:SS to seconds, and the data plotted.
3) FIG. 8 shows a typical plot of the sensor response for one cycle of test with purging and sampling periods. Slopes from the signal as a function of time are assessed for sampling and purging periods. Linear fitting was done for the purging period, which lasts about 60 seconds and the sampling period, which lasts for 6 seconds.
4) A sensor response was calculated as: Sensor response=$Slope_{sampling}$−$Slope_{purging}$. The value of the sensor response was proportional to the NO concentration.
5) For each test the subject was been tested three times for a total of three readings. The mean of these three readings was calculated.
6) The mean of each test was plotted along with the NO concentrations from the NO analyzer (i.e. the chemiluminescence equipment, gold standard) and linear fitting was applied. Then the linear fitting was used as an internal calibration curve.
7) Using the internal calibration curve obtained from step 6 the original NO sensor response (A.U./S) was converted to concentration (ppb).
8) A correlation plot for the sensor response (ppb) from the subject low back pressure mouthpiece NO device was made comparing the corresponding response from the commercially available device. Another plot comparing the subject device with the gold standard (the chemiluminescence equipment) was also evaluated.
9) Linear fitting was done to these plots. Then the "r" values were obtained from the linear fitting. An "r" value greater than 0.9, indicated that the subject NO device shows correlation of better than 90% with the commercial device.
10) Based on the linear fitting parameters, the residuals and the standard error of estimate can be calculated according to the following equations.
Predicted Values: $Y_i = A + B * X_i$
Where $X_i$ was the concentration from the comparative method; $Y_i$ was the predicted value according to the regression curve.
The residual was calculated by: Residual i=$y_i - Y_i$
Where $y_i$ was the corresponding concentration from the NO device.

The residuals were plotted against the corresponding concentration from the comparative method. And the standard error of the residuals was calculated for different range of NO concentrations: <50 ppb, 50-100 ppb, >100 ppb.

Figure 7:
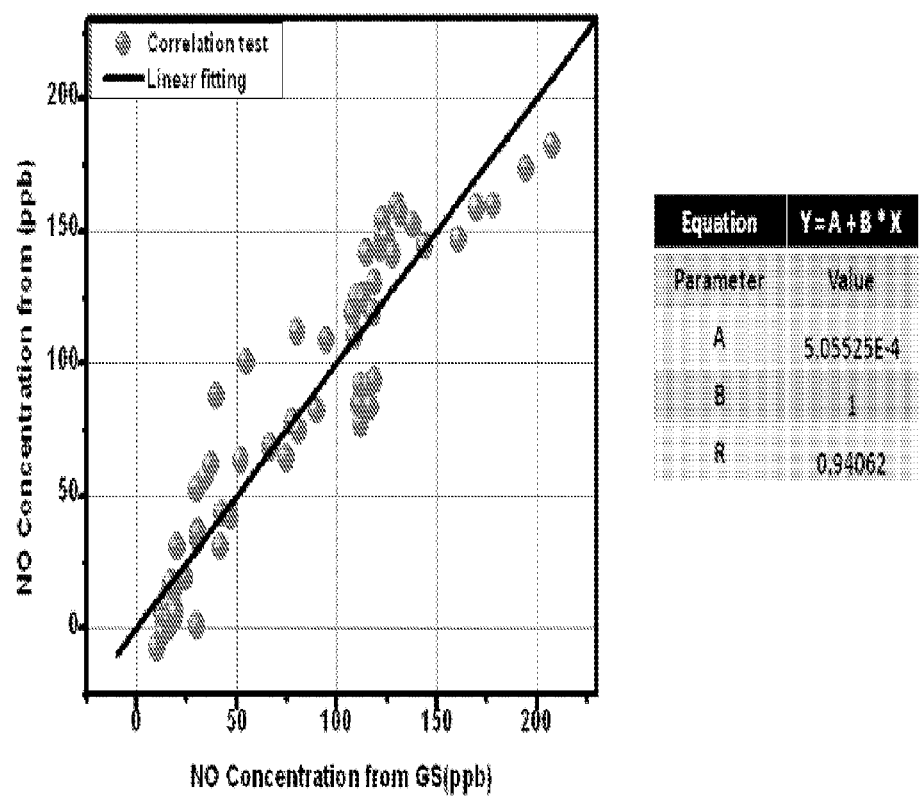
FIG. 7 graphically shows an example of a correlation plot between an NO device and gold standard method.

Referring now to FIG. 7 an example of a correlation plot between a subject NO device and the chemiluminescence equipment method is shown. Since the chemiluminescence technique is generally regarded as the gold standard of NO detection, this technique was used to measure the real concentration of NO sample. The graphical representation includes an ordinate representing NO concentration as read from a mouthpiece under test in ppb compared to an abscissa representing NO concentration from the gold standard in ppb. The data points (X, Y) represent actual correlation test values from a correlation of an NO device comprising a low back pressure mouthpiece constructed in accordance with the principles disclosed herein with a "gold standard" (GS) measurement of NO concentration. The curve 100 is a linear fitting of the data showing a residual value R of 0.94062.

Briefly, 9 different subjects with the exhaled nitric oxide (eNO) concentration in the range of 10-210 ppb were tested by the gold standard method, another commercial device, and the presently disclosed low back pressure mouthpiece to evaluate the correlations. The low back pressure mouthpiece was tested at ambient conditions, i.e. at room temperature, between 16° C. and 30° C., and a relative humidity (RH) between 20% and 60% (non-condensing).

The invention has been described herein in considerable detail in order to comply with the Patent Statutes and to provide those skilled in the art with the information needed to apply the novel principles of the present invention, and to construct and use such exemplary and specialized components as are required. However, it is to be understood that the invention may be carried out by different equipment, and devices, and that various modifications, both as to the equipment details and operating procedures, may be accomplished without departing from the true spirit and scope of the present invention.

REFERENCES

1. Kharitonov, S. et. al., "Exhaled and nasal nitric oxide measurements: recommendations," EUROPEAN RESPIRATORY JOURNAL, Volume: 10, Pages 1683-1693 Published: 1997.
2. Silkoff, P E et. al., "Marked flow-dependence of exhaled nitric oxide using a new technique to exclude nasal nitric oxide" AMERICAN JOURNAL OF RESPIRATORY AND CRITICAL CARE MEDICINE Volume: 155 Issue: 1 Pages: 260-267 Published: January 1997.
3. Kharitonov, Sergei A. et. al., "Nasal contribution to exhaled nitric oxide during exhalation against resistance or during breath holding," THORAX, Volume: 52 Pages: 540-544 Published 1997.
4. Hogman, M. et. al., "Nitric oxide from the human respiratory tract efficiently quantified by standardized single breath measurements," SCANDINAVIAN PHYSIOLOGICAL SOCIETY, Volume: 159, Pages: 345-346, Published: 1997.
5. Malmberg, L. P. et. al., "Exhaled nitric oxide rather than lung function distinguishes preschool children with probable asthma," THORAX, Volume: 58, Pages: 494-499, Published 1997.
6. American Thoracic Society and European Respiratory Society, "ATS/ERS Recommendations for Standardized Procedures for the Online and Offline Measurement of Exhaled Lower Respiratory Nitric Oxide and Nasal Nitric Oxide," AMERICAN JOURNAL OF RESPIRATORY AND CRITICAL CARE MEDICINE, Volume 171, Pages 912-930, Published, 2005.
7. Gustafsson, L. E. et. al., "Endogenous Nitric Oxide is Present in the Exhaled Air of Rabbits, Guinea Pigs and Humans, "BIOCHEMICAL AND BIOPHYSICAL RESEARCH COMMUNICATIONS, Volume: 181, Number: 2, Pages: 852-857, Published December 1991.
8. Persson, Magnus et. al., "Single-breath nitric oxide measurements in asthmatic patients and smokers," LANCET, Volume: 343, Pages: 146-147, Published: 1994.
9. Matsumoto, Akihiro et. al., "Increased Nitric Oxide in the Exhaled Air of Patients with Decompensated Liver Cirrhosis," ANN. INTERN MED., Volume: 123, Pages: 110-113, Published 1995.

What is claimed is:

1. A back pressure mouthpiece apparatus for detection of exhaled nitric oxide (NO), the apparatus comprising:
   an inlet conduit;
   an oxidizing filter housing having an inlet and an outlet, the oxidizing filter housing having an inner diameter fixed between 9.6 mm and 18 mm;
   a first filter located proximate the oxidizing filter housing inlet and a second filter located proximate the oxidizing filter housing outlet;
   filtering particles packed between the first and second filters, the filtering particles including $CaSO_4$ and an oxidant including a solid porous substrate impregnated with sodium permanganate;
   a coupler attaching the inlet conduit to the oxidizing filter housing inlet;
   an outlet tube coupled to the oxidizing filter housing outlet;
   where the oxidizing filter housing, first and second filters and filtering particles produce a flow resistance of less than 4 $H_2O$ cm;
   a sensor coupled to receive exhaled breath flowing from the inlet conduit through the outlet tube, where the sensor provides output data; and
   a pressure sensor coupled to the filter housing outlet, the pressure sensor having an output, electronics coupled to the pressure sensor output for calculating a pressure measurement and a display coupled to receive and display the pressure measurement of the exhaled breath so that the subject can respond by adjusting the force of the exhalation to maintain a stable pressure, and flow rate within plus and minus 10%.

2. The apparatus of claim 1, wherein the oxidizing filter housing comprises acrylic tubing.

3. The apparatus of claim 2 wherein the acrylic tubing has an inner diameter of between 9.6 mm and 18 mm.

4. The apparatus of claim 1 wherein the filtering particles including $CaSO_4$ are replaced by a desiccant selected from the group consisting of activated alumina, aerogel, benzophenone, bentonite clay, calcium chloride, calcium sulfate, cobalt(ii) chloride, copper(ii) sulfate, lithium chloride, lithium bromide, magnesium sulfate, magnesium perchlorate, molecular sieve, potassium carbonate, silica gel, sodium, sodium chlorate, sodium chloride, sodium sulfate, sucrose and combinations thereof.

5. The apparatus of claim 4 wherein the oxidant is selected from the group consisting of Purafil media, oxygen ($O_2$), ozone ($O_3$), hydrogen peroxide ($H_2O_2$), inorganic peroxides, fluorine ($F_2$), chlorine ($Cl_2$), halogens, nitric acid ($HNO_3$) and nitrate compounds, sulfuric acid ($H_2SO_4$), peroxydisulfuric acid ($H_2S_2O_8$), peroxymonosulfuric acid ($H_2SO_5$), chlorite, chlorate, perchlorate, halogen compounds, hypochlorite, hypohalite compounds, household bleach (NaClO), hexavalent chromium compounds, chromic acid, dichromic acid, chromium trioxide, pyridinium chlorochromate (PCC), chromate/dichromate compounds, permanganate compounds, potassium permanganate, sodium perborate, nitrous oxide ($N_2O$), silver oxide ($Ag_2O$), osmium tetroxide ($OsO_4$) and combinations thereof.

6. The apparatus of claim 1 wherein the first and second filters comprise at least two felt pieces.

7. The apparatus of claim 6 wherein the at least two felt pieces comprise polyester fiber.

8. A method for detection of components of exhaled breath from a subject comprising:
  blowing exhaled breath into an inlet conduit;
  positioning an oxidizing filter housing having an inlet and an outlet to receive the exhaled breath, the oxidizing filter housing having a fixed inner diameter between 9.6 mm and 18 mm;
  filtering the exhaled breath with a first filter located proximate the oxidizing filter housing inlet and a second filter located proximate the oxidizing filter housing outlet and filtering particles packed between the first and second filters, the filtering particles including $CaSO_4$ and an oxidant including a solid porous substrate impregnated with sodium permanganate;
  operating the oxidizing filter housing, first and second filters and filtering particles to produce a flow resistance of less than 4 $H_2O$ cm;
  sensing one or more components of the exhaled breath;
  sensing pressure of the exhaled breath to provide a pressure measurement; and
  displaying the pressure measurement so that the subject can respond by adjusting the force of the exhalation to maintain a stable pressure, and flow rate within plus and minus 10%.

9. The method of claim 8 wherein the filtering particles including $CaSO_4$ are replaced by a desiccant selected from the group consisting of activated alumina, aerogel, benzophenone, bentonite clay, calcium chloride, calcium sulfate, cobalt(ii) chloride, copper(ii) sulfate, lithium chloride, lithium bromide, magnesium sulfate, magnesium perchlorate, molecular sieve, potassium carbonate, silica gel, sodium, sodium chlorate, sodium chloride, sodium hydroxide, sodium sulfate, sucrose and combinations thereof.

10. The method of claim 9 wherein the oxidant is selected from the group consisting of Purafil media, oxygen ($O_2$), ozone ($O_3$), hydrogen peroxide ($H_2O_2$), inorganic peroxides, fluorine ($F_2$), chlorine ($Cl_2$), halogens, nitric acid ($HNO_3$) and nitrate compounds, sulfuric acid ($H_2SO_4$), peroxydisulfuric acid ($H_2S_2O_8$), peroxymonosulfuric acid ($H_2SO_5$), chlorite, chlorate, perchlorate, halogen compounds, hypochlorite, hypohalite compounds, household bleach (NaClO), hexavalent chromium compounds, chromic acid, dichromic acid, chromium trioxide, pyridinium chlorochromate (PCC), chromate/dichromate compounds, permanganate compounds, potassium permanganate, sodium perborate, nitrous oxide ($N_2O$), silver oxide ($Ag_2O$), osmium tetroxide ($OsO_4$) and combinations thereof.

11. The method of claim 8, wherein said one or more components is selected from the group consisting of carbon dioxide, oxygen, nitric oxide, nitrogen, nitrogen dioxide, hydrogen peroxide, proteins, surfactants, DNA, acetone, ammonia, sulfur compounds, acetylene, carbon monoxide, ethane and pentane.

12. The method of claim 8, wherein said one or more components consists essentially of nitric oxide.

\* \* \* \* \*